(12) United States Patent
Brunet

(10) Patent No.: US 11,696,849 B2
(45) Date of Patent: Jul. 11, 2023

(54) INTRAVAGINAL DEVICE

(71) Applicant: CNTRL+ INC., Cornwall (CA)

(72) Inventor: Karen Lesley Brunet, Cornwall (CA)

(73) Assignee: CNTRL+ INC., Cornwall (CA)

( * ) Notice: Subject to any disclaimer, the term of this patent is extended or adjusted under 35 U.S.C. 154(b) by 216 days.

(21) Appl. No.: 17/286,522

(22) PCT Filed: Jan. 13, 2021

(86) PCT No.: PCT/CA2021/050026
§ 371 (c)(1),
(2) Date: Apr. 19, 2021

(87) PCT Pub. No.: WO2021/142537
PCT Pub. Date: Jul. 22, 2021

(65) Prior Publication Data
US 2022/0133528 A1    May 5, 2022

Related U.S. Application Data

(60) Provisional application No. 62/960,839, filed on Jan. 14, 2020.

(51) Int. Cl.
*A61F 6/12*      (2006.01)
*A61B 17/42*   (2006.01)
*A61F 2/00*      (2006.01)
*A61B 17/00*   (2006.01)

(52) U.S. Cl.
CPC ............... *A61F 6/12* (2013.01); *A61B 17/42* (2013.01); *A61F 2/005* (2013.01); *A61B 2017/00805* (2013.01); *A61F 2230/0069* (2013.01)

(58) Field of Classification Search
CPC .............. A61F 6/08; A61F 6/12; A61F 2/005
See application file for complete search history.

(56) References Cited

U.S. PATENT DOCUMENTS

| | | | |
|---|---|---|---|
| 4,795,449 A | 1/1989 | Schneider et al. | |
| 6,090,098 A | 7/2000 | Zunker et al. | |
| 6,413,203 B1 | 7/2002 | Sahatjian | |
| 6,413,206 B2 | 7/2002 | Biswas | |
| 2004/0249238 A1* | 12/2004 | Farrell | A61F 2/005 600/29 |
| 2009/0266367 A1* | 10/2009 | Ziv | A61F 6/08 128/834 |
| 2016/0374788 A1* | 12/2016 | Ramachandra | A61F 6/08 600/29 |

FOREIGN PATENT DOCUMENTS

| | | |
|---|---|---|
| CA | 2657138 C | 1/2008 |
| CN | 201949183 U | 8/2011 |
| WO | 2012006670 A1 | 1/2012 |

* cited by examiner

*Primary Examiner* — Carrie R Dorna

(57) ABSTRACT

An intravaginal device that has a hollow open-ended cylindrical body and a removal strip, wherein the body has features that keep the removal strip in a track. During removal when the removal strip is pulled, the cross-sectional area of the device is decreased. A kit includes the device, removal strip and an assistive wand to aid with insertion and removal.

12 Claims, 15 Drawing Sheets

INTRAVAGINAL DEVICE

RELATED APPLICATION

This application is a United States National Phase under 35 U.S.C. § 371 of International Application No. PCT/CA2021/050026, filed on Jan. 12, 2021, which claims priority to, and the benefit of U.S. Provisional Patent Application No. 62/960,839, filed on Jan. 14, 2020, the contents of which are incorporated herein by reference in their entirety.

TECHNICAL FIELD

The present invention relates to intravaginal devices and uses thereof.

BACKGROUND

Stress urinary incontinence refers to the leakage of urine because of increased pressure placed on the bladder by for example coughing, sneezing, laughing, exercising or lifting something heavy. It is the most common cause of urinary incontinence in women and significantly impacts the quality of life of women suffering from this problem.

Female overactive bladder refers to a frequent and urgent need to urinate, which can come on quite suddenly. The signal that the bladder needs emptying may occur even if the bladder is only partially full.

Incomplete bladder emptying refers to a condition where after voiding as much as possible, the bladder retains some urine. It may be caused by the position of the bladder relative to the urethra due to prolapse.

Pelvic organ prolapse is the descent of one or more of the pelvic structures (bladder, uterus, vagina, colon, rectum) from the normal anatomic location toward or through the vaginal opening. Pelvic organ prolapse may occur when the pelvic floor muscles and ligaments stretch and weaken and no longer provide enough support for the pelvic structures. Pelvic organ prolapse may be associated with stress urinary incontinence.

While there are surgical options to treat stress incontinence and pelvic organ prolapse, such as sling procedures and colposuspension, significant risks and complications may arise. Given these risks and complications, non-surgical approaches are often used for the management of stress urinary incontinence and pelvic organ prolapse.

A device, a vaginal pessary, may be inserted into the vagina to aid in controlling stress urinary incontinence and/or support the prolapsed structures. A variety of vaginal pessaries are known in the art and include but are not limited to ring and shelf pessaries.

U.S. Pat. No. 6,413,206B2 describes an intravaginal device to aid in controlling urinary incontinence by engaging the anterior vaginal wall to support the vaginal wall and the urethra there behind.

SUMMARY

An object of the present invention is to provide an intravaginal device.

In accordance with an aspect of the present invention, there is provided an intravaginal device comprising a hollow open-ended cylindrical body and a removal strip; the body having a first end and a second end, an anterior wall and a posterior wall; the body having a first notch in the first end of the anterior wall, and a second notch in the second end of the anterior wall wherein the first notch and the second notch positioned in line and substantially at the midline of the anterior wall and forming a track for the removal strip; the posterior wall comprising a lingulate-shaped extension, and an opening positioned substantially across from the first notch wherein the opening is adapted to receive therethrough the removal strip; wherein the removal strip passes through the first notch, second notch and opening and when force is applied to the removal strip the anterior wall and the posterior wall are compressed together.

In accordance with another aspect of the present invention, there is provided an intravaginal device comprising a hollow open-ended cylindrical body and a removal strip; the body formed from a non-absorbent, flexible material; the body having a first end and a second end, an anterior wall and a posterior wall; the posterior wall comprising a lingulate-shaped extension; the body having a first notch in the first end in the anterior wall and second notch in the second end in the anterior wall; the first notch and the second notch positioned in line and substantially at the midline of the anterior wall and forming a track for the removal strip; the posterior wall further comprising an opening adapted to receive therethrough the removal strip and the opening positioned substantially across from the first notch; the removal strip formed from a non-absorbent, flexible material; wherein the removal strip passes through the first notch, second notch and opening and compresses the anterior wall and the posterior wall together thereby reducing the cross-sectional area of the body when force is applied to the removal strip.

In accordance with another aspect of the present invention, there is provided the use of the intravaginal device of the invention to aid in the control of female urinary stress incontinence.

In accordance with another aspect of the present invention, there is provided the use of the intravaginal device of the invention to aid pelvic organ prolapse.

In accordance with another aspect of the present invention, there is provided the use of the intravaginal device of the invention to aid rectocele.

In accordance with another aspect of the present invention, there is provided a method of controlling female urinary stress incontinence, comprising inserting the device of the invention into the vagina.

In accordance with another aspect of the present invention, there is provided a method of aiding pelvic organ prolapse comprising inserting the device of the invention into the vagina.

In accordance with another aspect of the present invention, there is provided a method of aiding rectocele, comprising inserting the device of the invention into the vagina.

In accordance with another aspect of the present invention, there is provided a method of controlling female overactive bladder, comprising inserting the device of the invention into the vagina.

In accordance with another aspect of the present invention, there is provided a method of controlling female incomplete bladder emptying, comprising inserting the device of the invention into the vagina.

In accordance with another aspect of the present invention, there is provided a kit comprising the intravaginal device of the invention, removal strip and instructions.

In accordance with another aspect of the present invention, there is provided a kit comprising the intravaginal device of the invention, an assistive wand, removal strip and instructions.

BRIEF DESCRIPTION OF THE FIGURES

These and other features of the invention will become more apparent in the following detailed description in which reference is made to the appended drawings.

DETAILED DESCRIPTION

Figure 1:
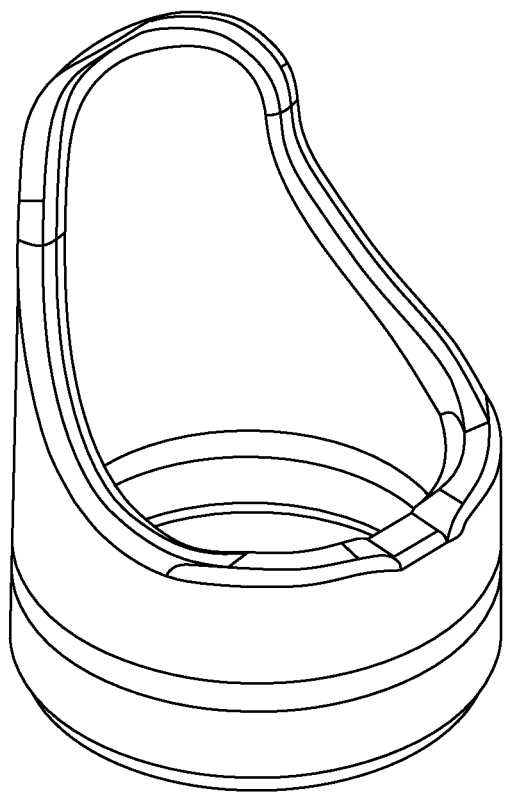
FIG. 1 illustrates a perspective view of the intravaginal device of an embodiment of the present invention.
Figure 2:
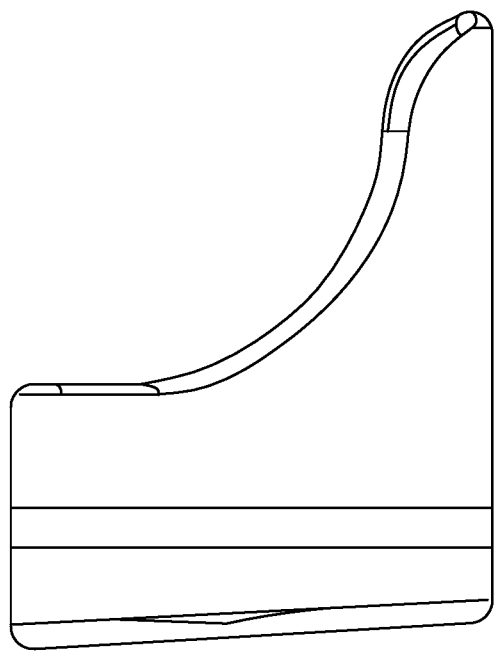
FIG. 2 illustrates a side view of the intravaginal device illustrated in FIG. 1.
Figure 3:
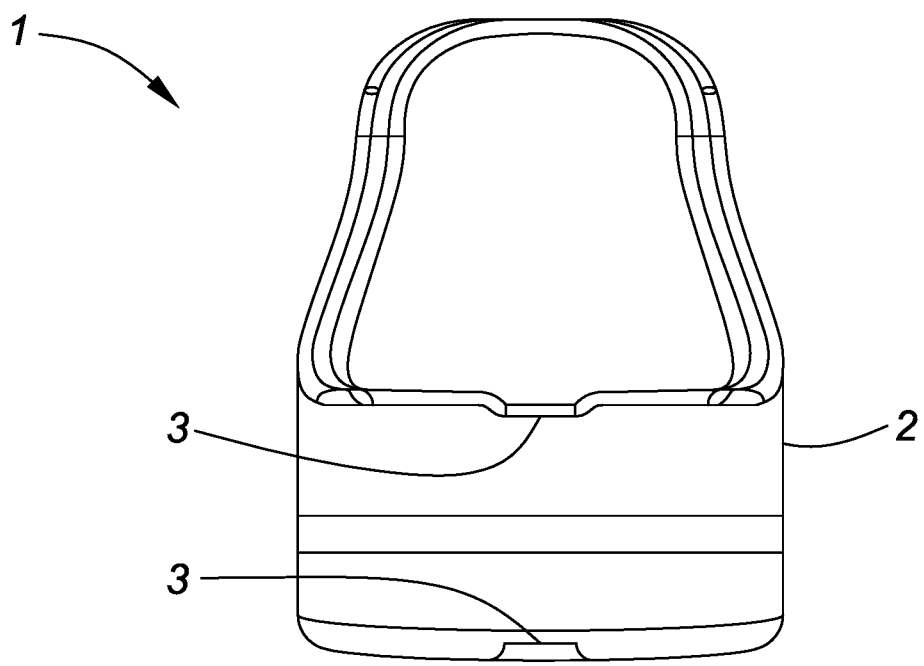
FIG. 3 illustrates the front view of the intravaginal device illustrated in FIG. 1.
Figure 4:
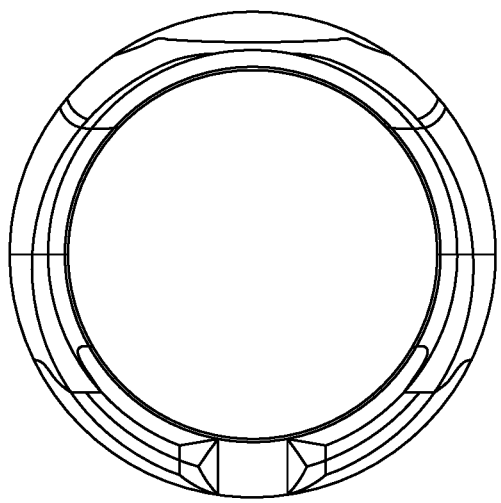
FIG. 4 illustrates the cross-sectional view of the bottom end of the intravaginal device illustrated in FIG. 1.
Figure 5:
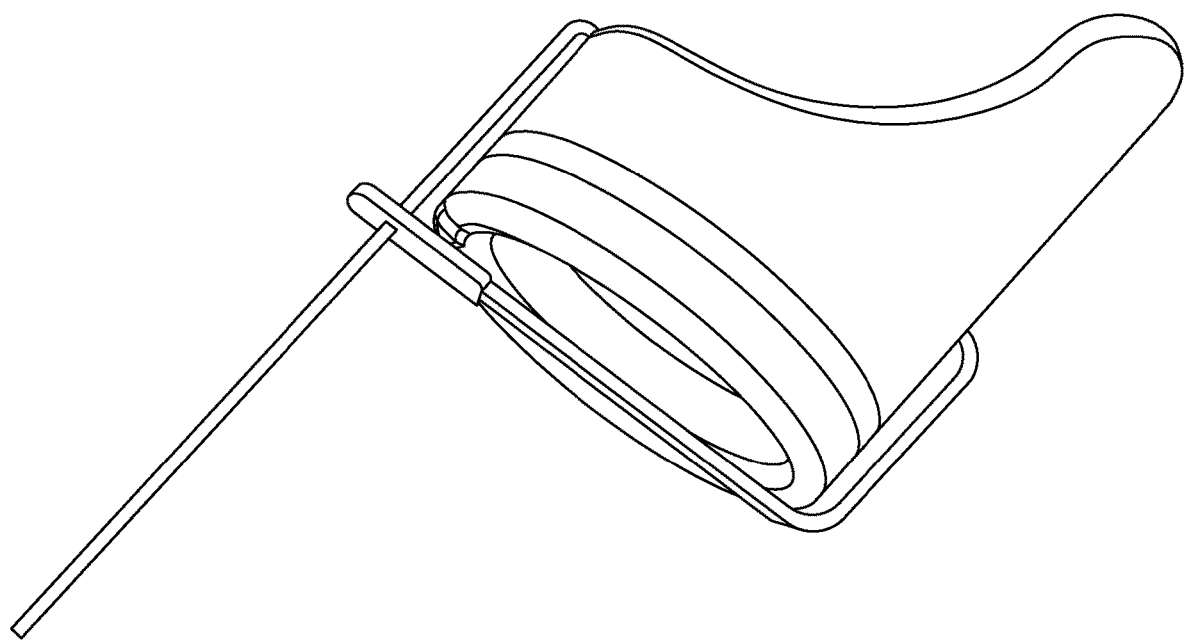
FIG. 5 illustrates a 3D view of an embodiment of an intravaginal device with removal strip.
Figure 6A:
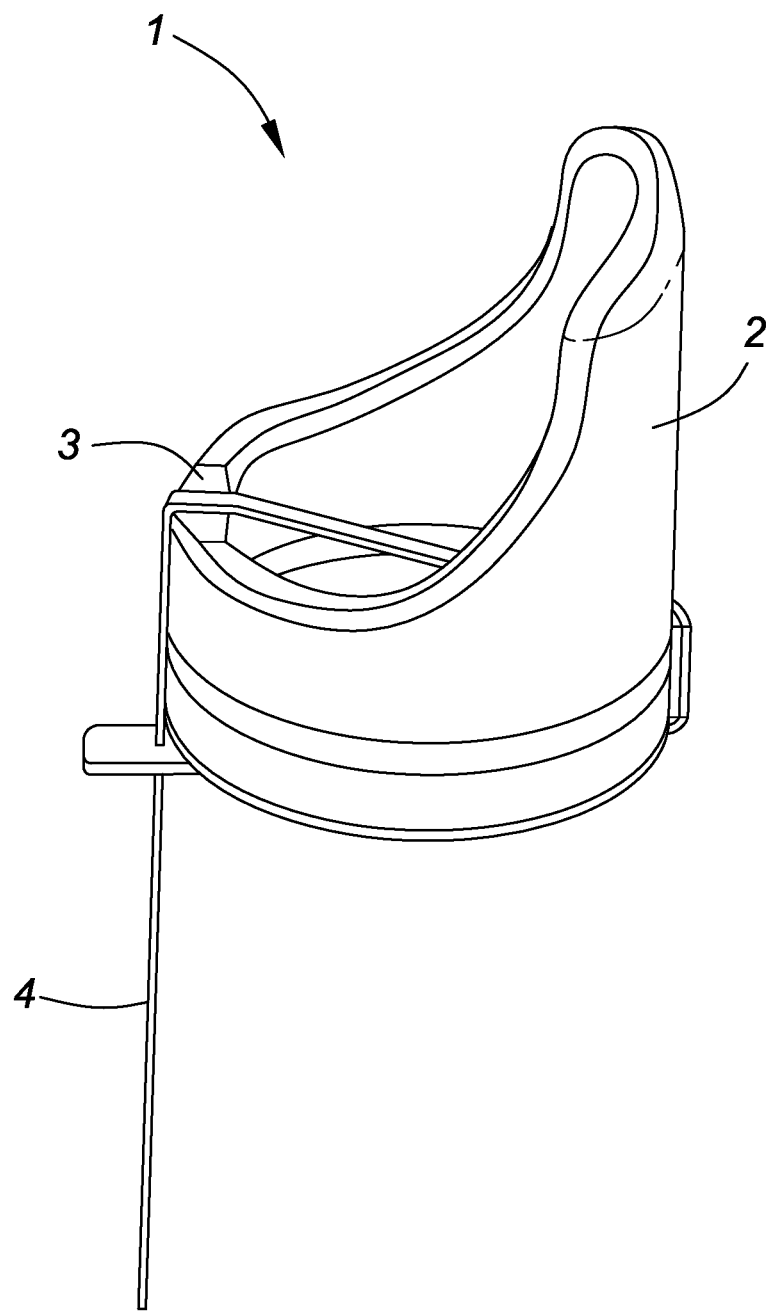
FIG. 6A illustrates an alternative view of the intravaginal device illustrated in FIG. 5.
Figure 6B:
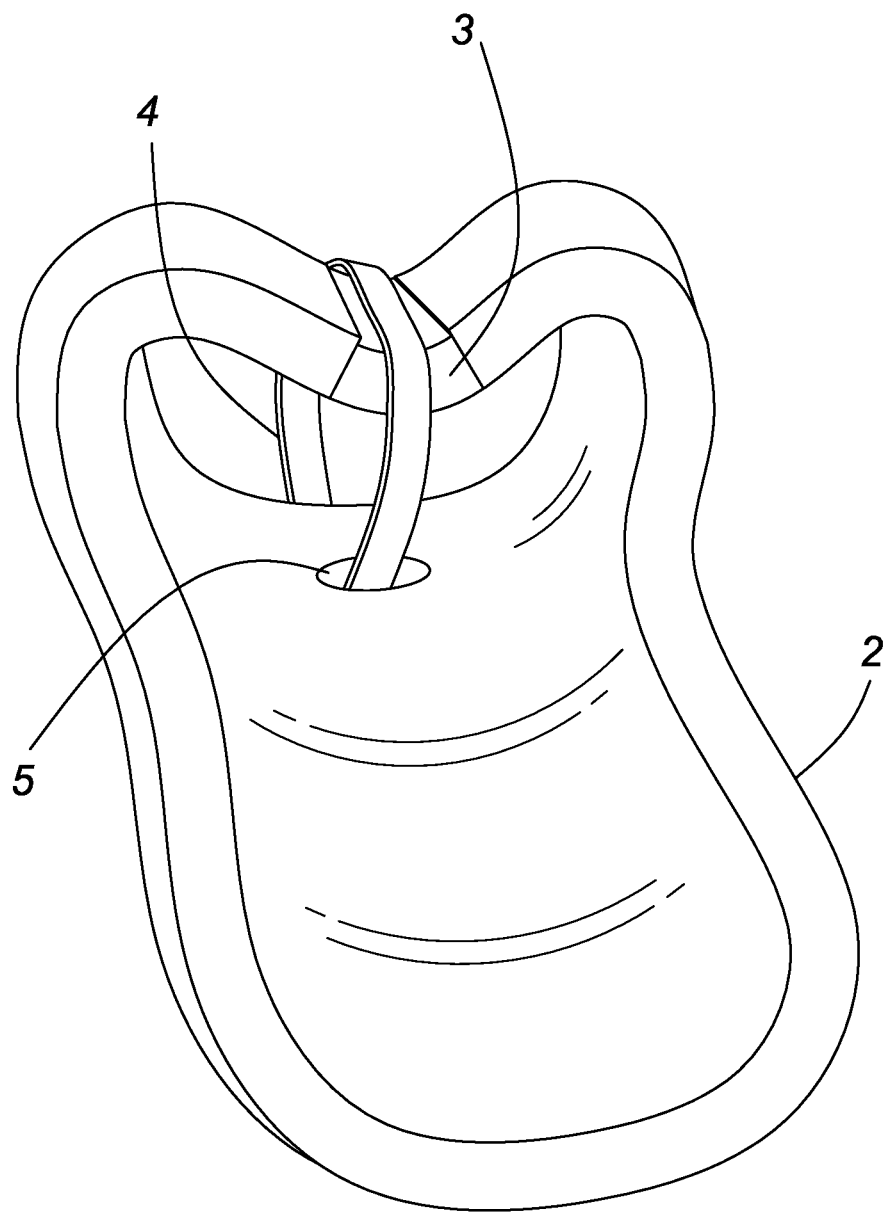
FIG. 6B illustrates an alternative view of the intravaginal device illustrated in FIG. 5.
Figure 7:
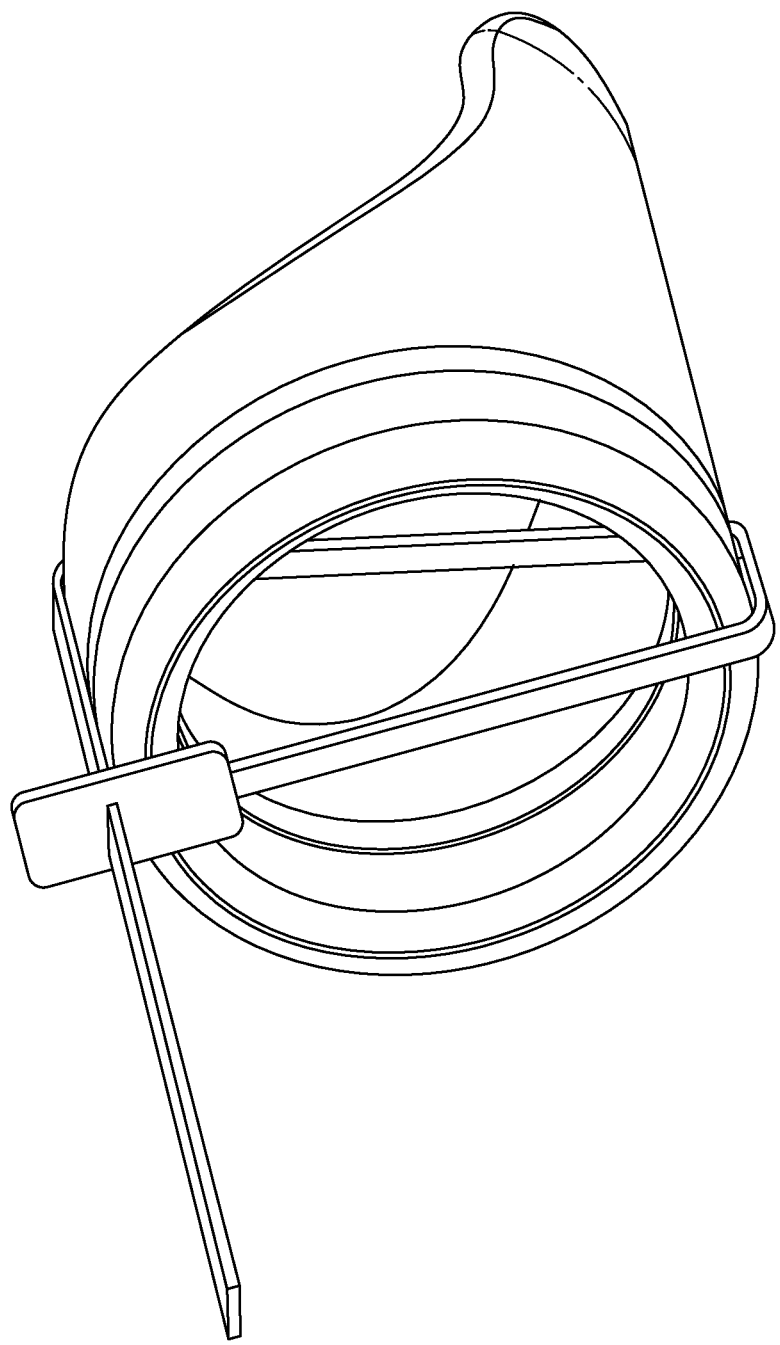
FIG. 7 illustrates an alternative view of the intravaginal device illustrated in FIG. 5.
Figure 8:
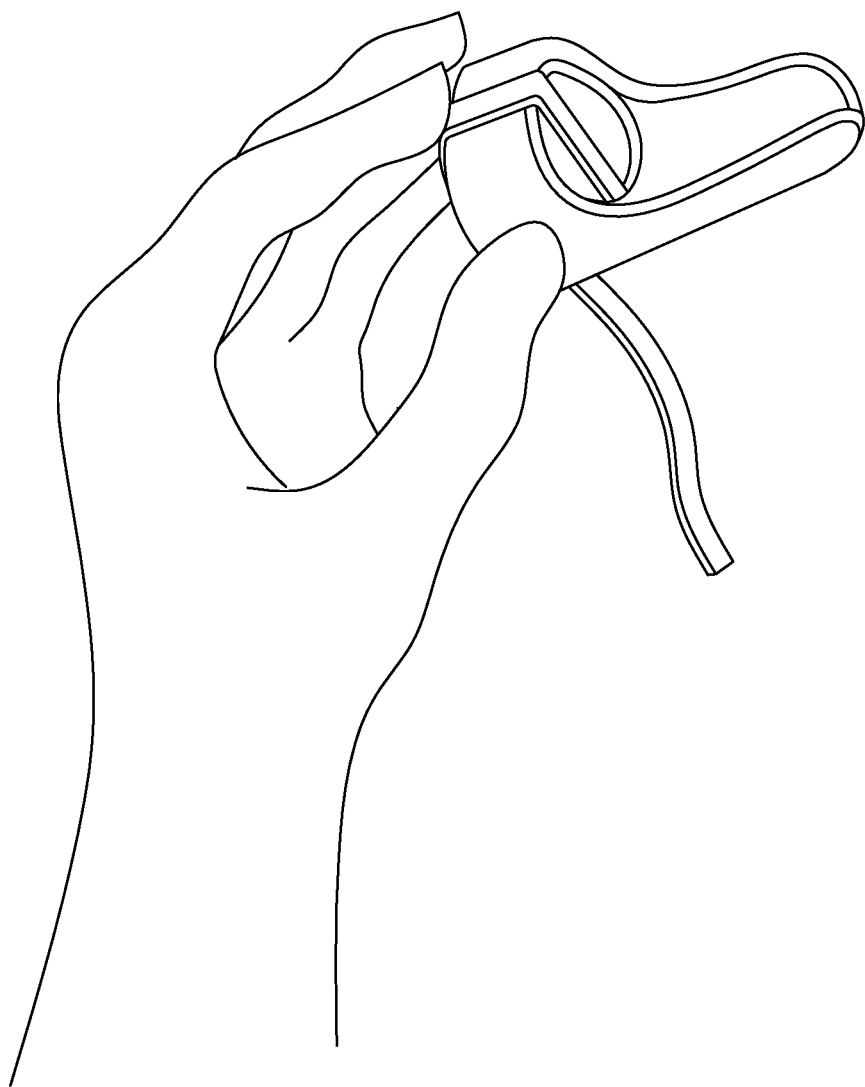
FIG. 8 is a line drawing of a hand holding the intravaginal device of an embodiment of the present invention.
Figure 9:
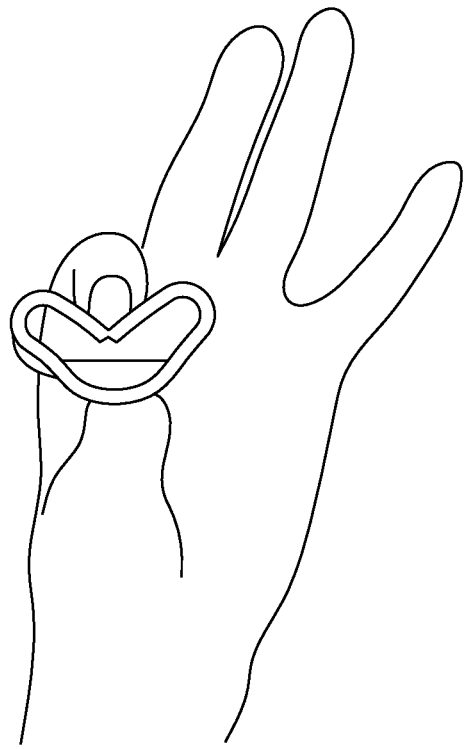
FIG. 9 is a line drawing of a hand holding the intravaginal device of an embodiment of the present invention being compressed.
Figure 10:
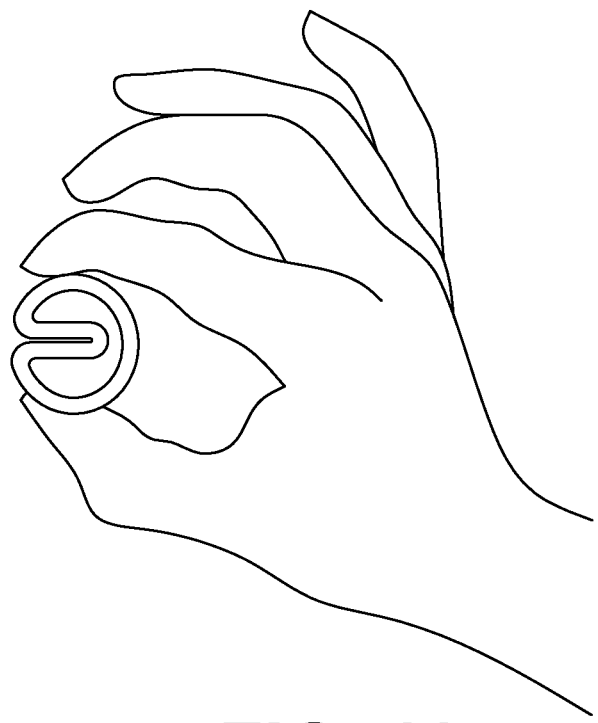
FIG. 10 is a line drawing of an intravaginal device of an embodiment of the present invention being compressed.
Figure 11:
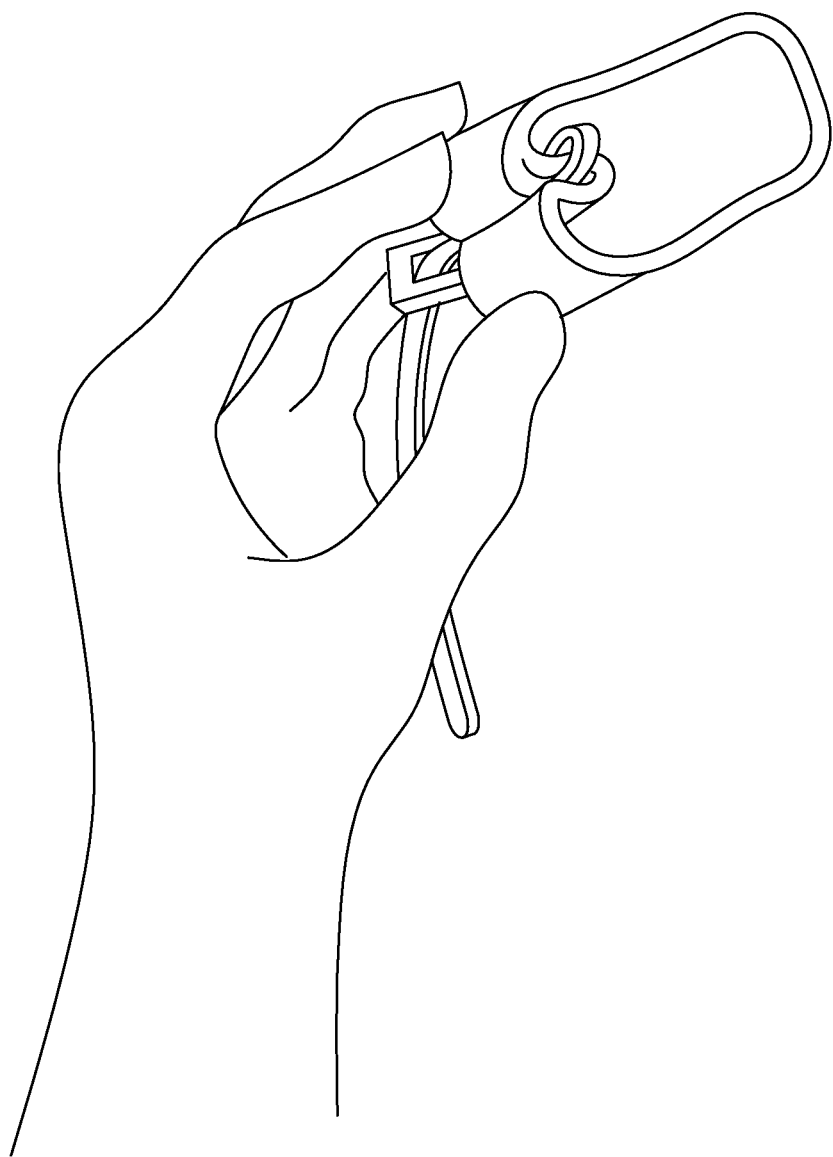
FIG. 11 is a line drawing of an intravaginal device of an embodiment of the present invention being compressed.

The present invention provides an intravaginal device to aid in controlling stress urinary incontinence and/or overactive bladder and/or incomplete bladder emptying and/or to support pelvic organ(s) in a subject in need thereof, for example in a subject with or at risk of pelvic organ prolapse.

Intravaginal Device

The intravaginal device 1 of the present invention comprises a body 2 for engaging and supporting the vaginal walls and a removal strip 4. See FIGS. 1 to 18D.

The Body of the Intravaginal Device:

The body 2 of the intravaginal device is formed from a non-absorbent (optionally hydrophobic) and flexible material. By using non-absorbent (optionally hydrophobic), material, the risk of odors developing, bacterial growth and toxic shock syndrome may be reduced. In certain embodiments, the non-absorbent material is washable and therefore, in such embodiments, the device is reusable. In other embodiments, the device is disposable.

Exemplary non-absorbent, flexible materials include but are not limited to thermoplastic elastomers such as thermoplastic vulcanizates. In certain embodiments, the body of the intravaginal device is made of a non-hygroscopic thermoplastic vulcanizate. In specific embodiments, the body is made of fully dynamically vulcanized EPDM (ethylene propylene diene monomer) runner in a thermoplastic matrix of polypropylene (PP) such as SANTOPRENE™. Exemplary grades of SANTOPRENE™ which may be used for the manufacture of the body include SANTOPRENE™ 8281-55MED.

The body 2 of the intravaginal device is shaped to engage the anterior vaginal wall and thereby support and elevate the anterior wall and urethra without closing the urethra and impeding urination. The body 2 further engages the posterior vaginal wall. In one embodiment, the device applies pressure to a weak vaginal wall where, in the absence of the device, a pelvic organ pushes into the vaginal cavity and creates a bulge. In one embodiment, the orientation of the device in the vagina is appropriate to support an anterior or posterior vaginal wall that is weak.

In certain embodiments, the body 2 is a hollow open-ended cylindrical body (ring) in which the posterior wall is extended in the first end to form a substantially lingulate-shaped extension. The lingulate-shape extension prevents the device from rotating and becoming displaced when inserted. In certain embodiments, the second end of the body has a slight inclination towards the posterior of the body portion. In certain embodiments, the inclination is between 1-5°. In specific embodiments, the inclination is 4°.

In certain embodiments, the body 2 includes one or more means to engage the removal strip. Non-limiting examples of means to engage the removal strip (4) include but are not limited to one or more notches (3), cut outs, openings (5) and combinations thereof. In specific embodiments, the body comprises a first notch in the first end in the anterior wall and second notch in the second end in the anterior wall; the first notch and the second notch being positioned in line and substantially at the midline of the anterior wall and forming a track for the removal portion; and the posterior wall further comprising an opening (5) adapted to receive therethrough the removal strip and the opening positioned substantially across from the first notch.

In certain embodiments, the intravaginal device includes one or more areas, flex points (6), to enhance the flexibility of the device. The areas which enhance flexibility may include for example areas of decreased thickness in the wall of the intravaginal device including but not limited to grooves, holes, cutouts or cuts in the wall of the intravaginal device. The one or more flex points may assist with preventing excess pressure being exerted against the urethra by the intravaginal device, thus preventing the possibility of urination being obstructed. The one or more areas may assist with the collapse or folding of the intravaginal device during insertion and removal of the device from the vagina. In specific embodiments, the device comprises a flex point on the interior anterior wall of the intravaginal device. In more specific embodiments, the flex point comprises a shallow cut located (see FIGS. 9 and 16B) on the interior anterior wall of the intravaginal device. In specific embodiments, the depth of the cut on the anterior inside bridge ranges from about 2 mm to about 4 mm. In particular embodiments, the depth of the cut is dependent on device size. For example, depth of 2 mm for small, 3 mm for medium and 4 mm large devices. In specific embodiments, the length of the cut is about 3 mm.

Removal Strip

The intravaginal device further comprises a removal strip which may be used to assist with removal of the intravaginal device. See FIGS. 18A-18D as well as FIGS. 5-7. The removal strip 4 may include for example one or more ribbons, strings and/or strips. In certain embodiments, the removal strip is constructed from non-absorbent material. In specific embodiments, the removal strip is a removal ribbon formed from a non-absorbent, flexible material. Exemplary materials include but are not limited to silicon.

In certain embodiments, pulling of the removal strip 4 decreases the cross-sectional area of the intravaginal device. In specific embodiments, the cross-sectional area is decreased by collapsing the anterior wall into the posterior wall or vice versa. In certain embodiments, the removal strip 4 is attached to the device body 2. In other embodiments, the removal strip 4 is associated but not anchored to the body 2. For example, the removal strip 4 may be looped around/through the body 2. In certain embodiments, the removal strip passes through one or more notches 3 and/or openings 5 in the body 2, wherein the one or more notches 3 and/or openings 5 are configured such that when force is applied the cross-sectional area of the body is reduced. In specific embodiments, at least one end of the removal strip comprises a stopper to prevent it from passing through one or more opening in the body. In specific embodiments one end of the removal strip 4 is inserted through an opening 14 in the second end of the removal strip thereby forming a loop which can be tightened when downward force is applied to the first end and thereby reducing the cross-sectional area of the body. In one embodiment both ends of the removal strip 4 have an opening 14. The opening in each end may be the same or different sizes and/or shapes. For example, the opening in the first end may be configured to allow insertion of a tool to aid in the removal of the device and the opening in second end may be configured to allow the first end of the removal strip to be inserted through the opening in the second and thereby form a loop. When the device is desired to be removed, the first end of the removal strip, which extends out of the vagina, can be pulled manually or by using a hook such as the hook end of an assistive wand. Once force is applied to the removal strip, the cross-sectional area of the body of the device is reduced to aid with removal. Or, removed by inserting an index finger through the anterior bridge of the device and pulling downward.

In certain embodiments, in which both ends of the removal strip 4 have openings, the hook can be inserted into the opening 14 in the first end of the removal strip which extends out of the vagina.

In certain embodiments, the removal strip 4 is a removal ribbon which is attached through the posterior hole or opening 5 and wrapped over the anterior bridge within the notches 3. See FIGS. 5 to 7.

Kits

In certain embodiments, a kit is provided that comprises the intravaginal device of the present invention, a removal strip, an assistive wand, and instructions. In certain embodiments, the instructions are provided through a website or digital material.

Figure 17A:
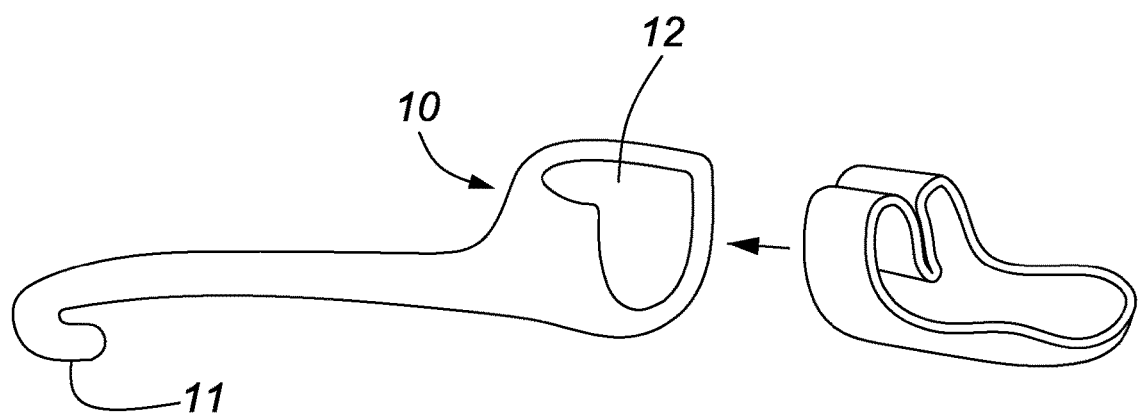
FIG. 17A is a line drawing of an assistive wand for use during insertion and removal of intravaginal device, and an intravaginal device of an embodiment of the present invention.
Figure 17B:
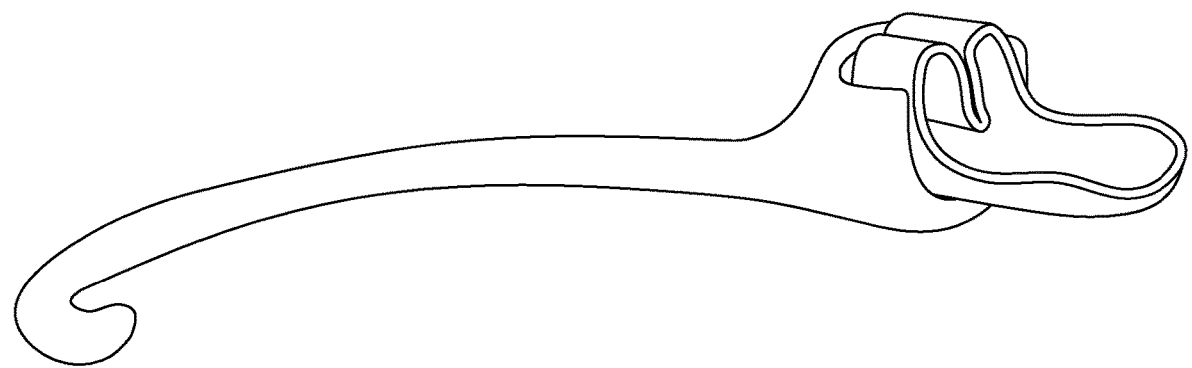
FIG. 17B is a line drawing of an assistive wand for use during insertion and removal of intravaginal device, and an intravaginal device of an embodiment of the present invention.
Figure 17C:
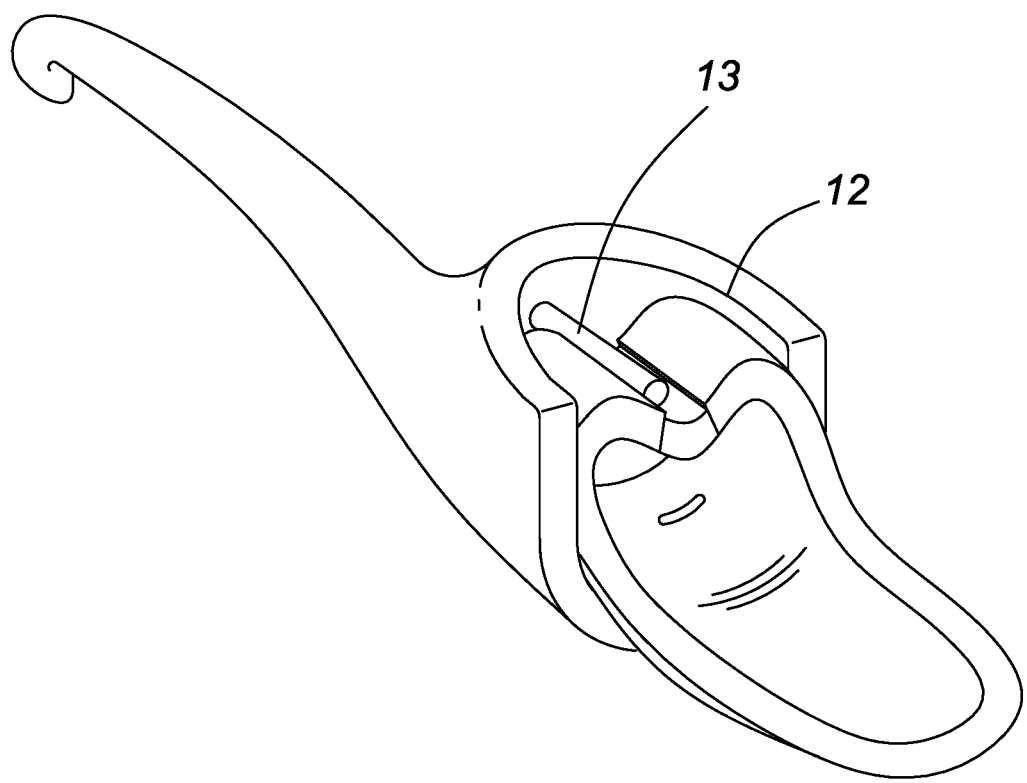
FIG. 17C is a line drawing of an assistive wand for use during insertion and removal of intravaginal device, and an intravaginal device of an embodiment of the present invention.
Figure 18A:
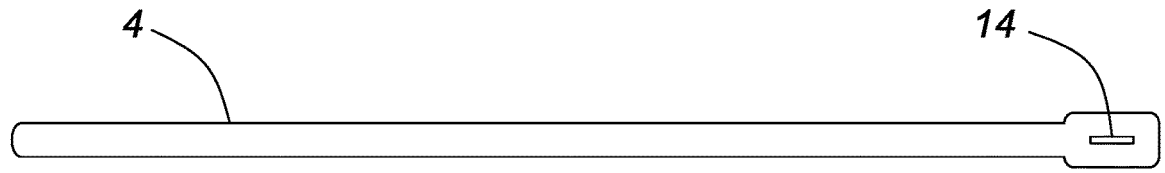
FIG. 18A is a line drawing of a removal strip of an embodiment of the present invention.
Figure 18B:
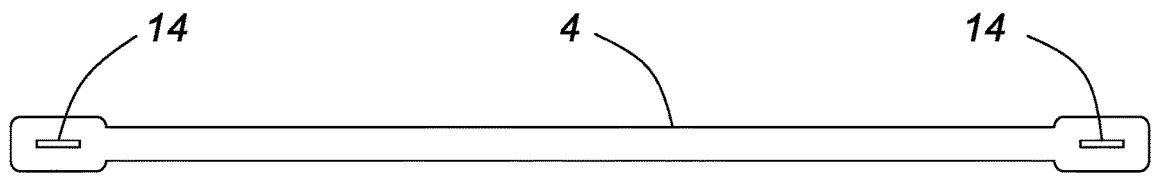
FIG. 18B is a line drawing of a removal strip of an embodiment of the present invention.
Figure 18C:
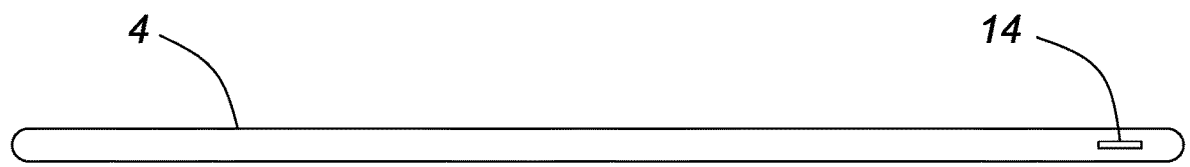
FIG. 18C is a line drawing of a removal strip of an embodiment of the present invention.
Figure 18D:
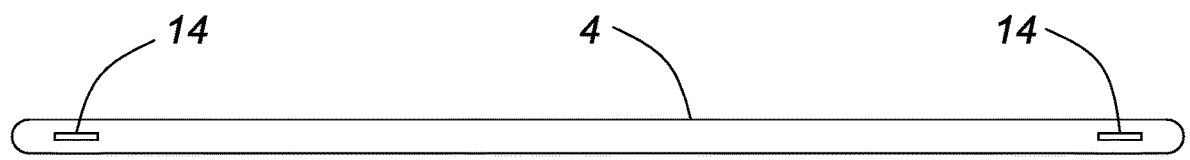
FIG. 18D is a line drawing of a removal strip of an embodiment of the present invention.

Illustrative embodiments of the assistive wand 10 are show in FIGS. 17A-17C. In certain embodiments, the assistive wand is an elongate member having a hook 11 end and a bowl 12 end. The hook end may be used to facilitate the removal of the intravaginal device. In particular, the hook may be used to grab the device by the removal strip 4 or by the body 2 of the device. In certain embodiments, the bowl 12 end of the assistive wand is able to hold the body of the intravaginal device in a collapsed position. It is easier to insert the device when it is in its collapsed position. Accordingly, in certain embodiments, the assistive wand may be used to facilitate insertion of the intravaginal device. In some embodiments, the assistive wand includes a rod 13 that maintains the intravaginal device in its collapsed position while it is located in the bowl 12 end of the assistive wand 10.

Methods and Uses

Figure 12:
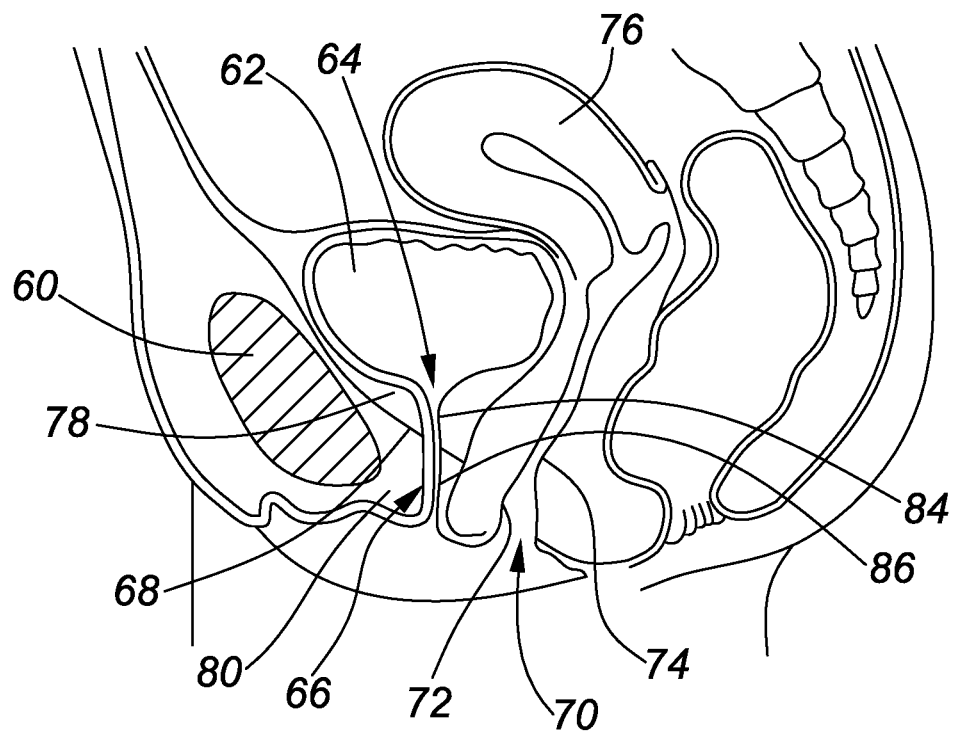
FIG. 12 is a sagittal abdominal cross-sectional view of a female patient illustrating the normal physiology of the bladder and urethra.

The normal anatomy of the urinary system of a female patient is shown in FIG. 12 including pubic bone 60, vaginal opening 70, anterior vaginal wall 72, posterior vaginal wall 74, and uterus 76. In normal anatomy, the bladder 62 is located such that the bladder neck 64 is positioned above the pelvic floor 68. The upper portion 84 of the urethra 66 lies within the abdominal cavity 78, and the lower portion 86 of the urethra lies within the vaginal cavity 80. As a consequence of the upper portion 84 of the urethra 66 lying within the abdominal cavity 78, when dynamic abdominal pressure is exerted, such as by exercise or by coughing, the abdominal pressure is exerted not only on the bladder 62 but also on the upper portion 84 of the urethra 66. This transient pressure on the upper portion 84 of the urethra 66 balances the pressure exerted on the bladder 62 and thus helps prevent the leakage of urine despite transient increased bladder pressure.

Figure 13:
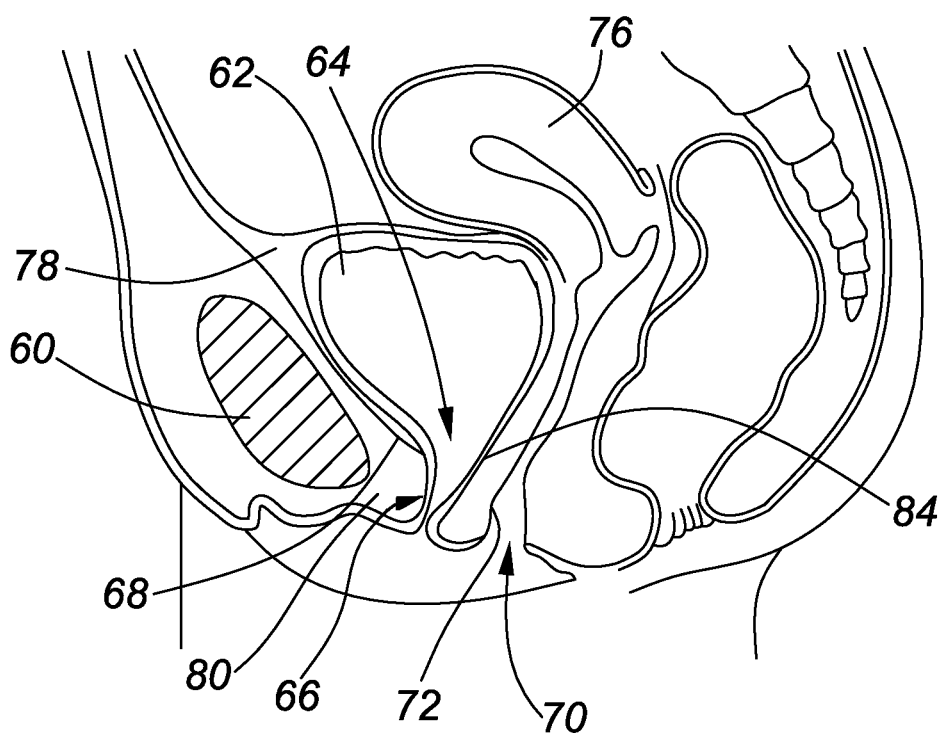
FIG. 13 is a sagittal abdominal cross-sectional view of an incontinent female patient with the bladder neck in a descended position.
Figure 14:
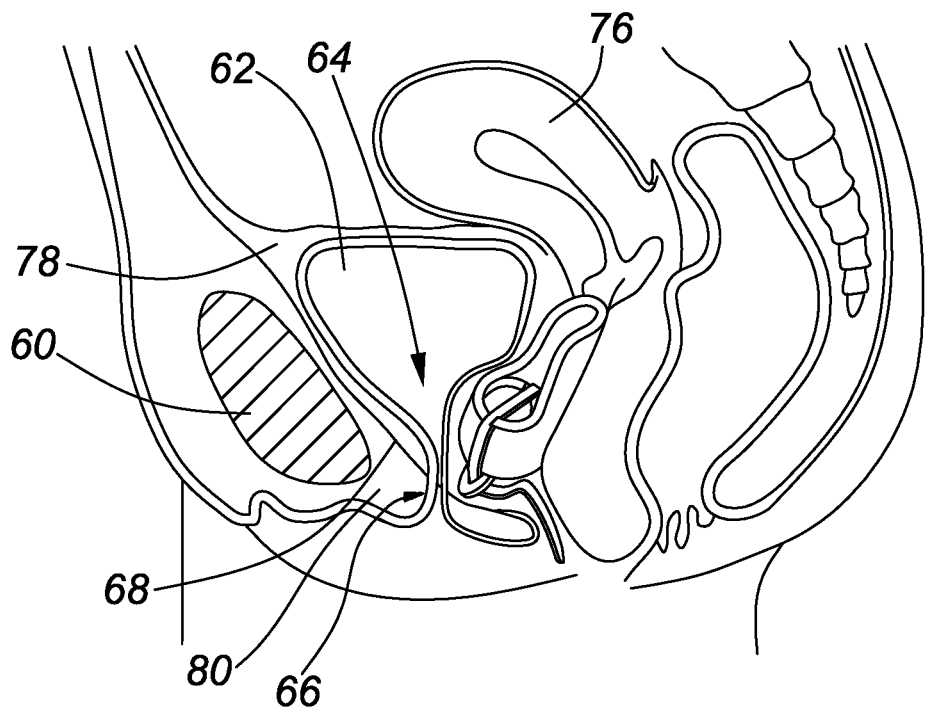
FIG. 14 is a sagittal abdominal cross-sectional view of the female patient of FIG. 13 showing the device of an embodiment of the present invention inserted.
Figure 15:
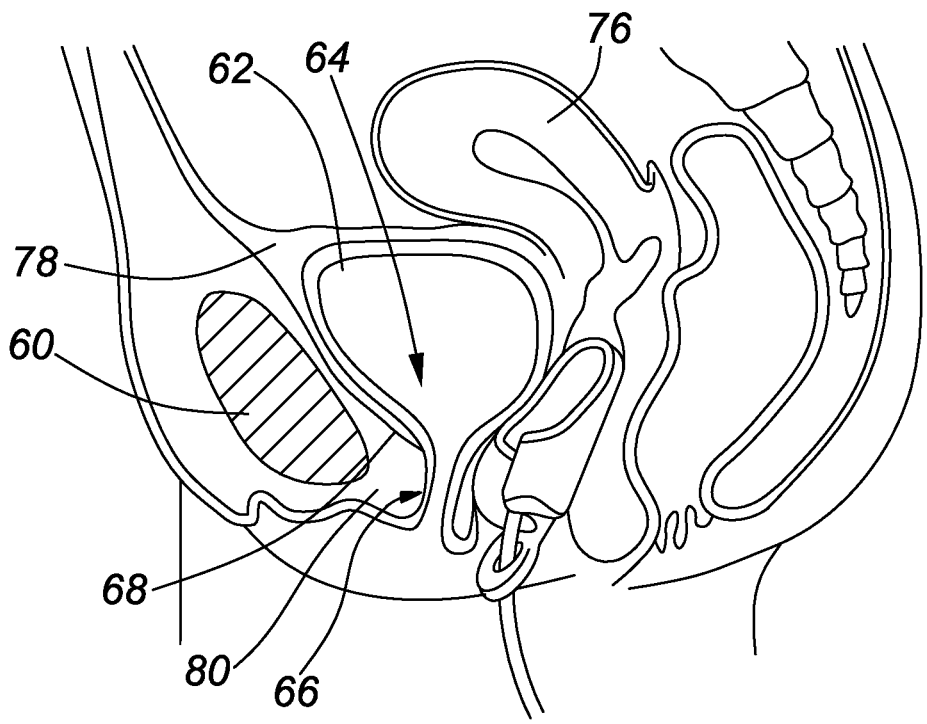
FIG. 15 is a sagittal abdominal cross-sectional view of the female patient of FIG. 14 showing the device of an embodiment of the present invention compressed for removal.
Figure 16A:
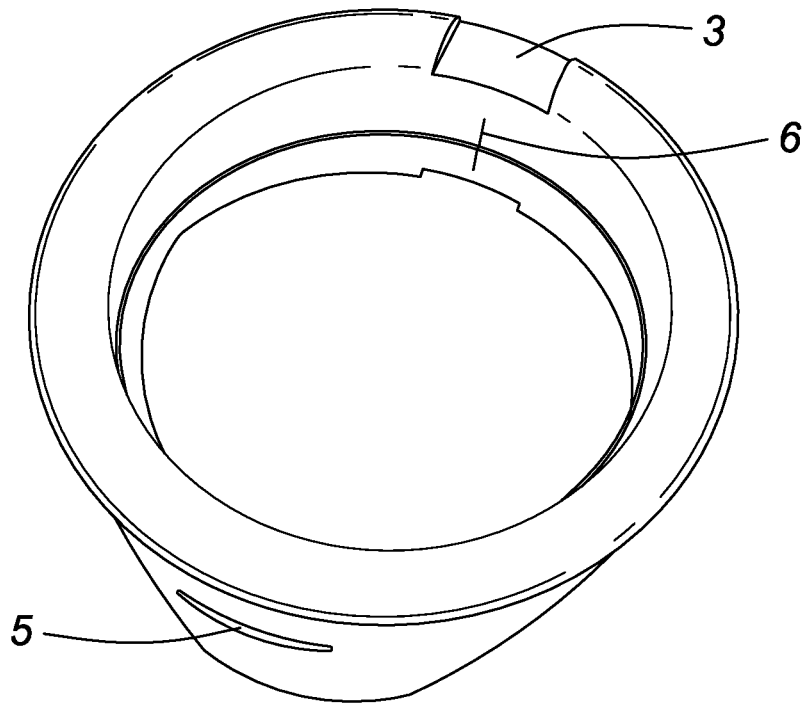
FIG. 16A is a line drawing of an intravaginal device of an embodiment of the present invention.
Figure 16B:
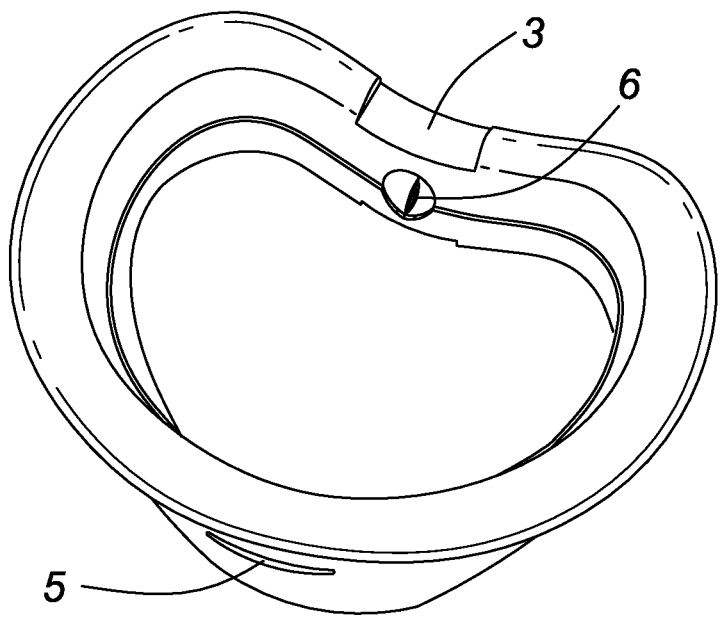
FIG. 16B is a line drawing of an intravaginal device of an embodiment of the present invention slightly compressed.

The anatomy of the urinary system of an incontinent female patient is illustrated in FIG. 13. In such patients, the bladder neck is in a descended position such that it is at a location at or below the pelvic floor 68. The entire urethra 66 lies within the vaginal cavity 80. In this condition, when dynamic abdominal pressure is exerted, because the upper portion 84 of the urethra 66 no longer lies within the abdominal cavity 78, there is no increased pressure exerted on the urethra 66 to offset the transient increased bladder pressure. Consequently, urine will leak when dynamic abdominal pressure is exerted, a condition known as stress urinary incontinence.

When installed in the vagina (see FIG. 14), the device corrects improper position of the urethra. In particular, the posterior wall of the body rests on the posterior vaginal wall and the anterior wall displaces the anterior vaginal wall forward and upward to support the urethra. This support stabilises a hypermobile urethra such that the upper portion of the urethra is retained within the abdominal cavity. Consequently, when a dynamic abdominal pressure is exerted, a portion of the abdominal pressure is applied against the upper portion of the urethra, which provides an additional force to offset transient bladder pressure increases.

Accordingly, in certain embodiments, there is provided a method of controlling stress urinary incontinence, the method comprising inserting the device of the present invention into the vagina of a subject in need thereof.

The intravaginal device of the present provides support for pelvic organ(s). Accordingly, in certain embodiments, may be used to support pelvic organ(s) in a subject in need thereof, for example in a subject with or at risk of pelvic organ prolapse. In certain embodiments, the intravaginal device of the present invention helps prevent, manage and slow the progression of prolapse. In certain embodiments, use of the intravaginal device alleviates one or more symptoms of pelvic organ prolapse.

A worker skilled in the art would readily appreciate that the use of an intravaginal device to support pelvic organ(s) in a subject having pelvic organ prolapse may be dependent on the severity of the pelvic organ prolapse. In certain embodiments, the pelvic organ prolapse is stage 1 pelvic organ prolapse. In certain embodiments, the pelvic organ prolapse is stage 2 pelvic organ prolapse.

A worker skilled in the art would further appreciate that the use of an intravaginal device to support pelvic organ(s) in a subject having pelvic organ prolapse may be dependent on that the type of pelvic organ prolapse. Types of pelvic organ prolapse include: cystocele (i.e. prolapse of the bladder into the vagina), urethrocele (i.e. prolapse of the urethra), uterine prolapse, vaginal vault prolapse, enterocele (i.e. a small intestine prolapse) and rectocele (i.e. prolapse of the posterior vaginal wall between the vagina and the rectum).

In certain embodiments, the pelvic organ prolapse is selected from one or more of the following cystocele, urethrocele, uterine prolapse, vaginal vault prolapse, enterocele and rectocele.

In certain embodiments, the pelvic organ prolapse is cystocele.

In certain embodiments, the pelvic organ prolapse is urethrocele.

In certain embodiments, the pelvic organ prolapse is rectocele. When in place in the vagina, the posterior wall of the intravaginal device rests against the posterior wall of the vagina and helps to support the weakened or thin wall of tissue that separates the vagina and rectum. That is, the intravaginal device of the present invention applies pressure to the posterior vaginal wall (as well as applying pressure to the anterior wall between the urethra and the vagina). This posterior pressure is helpful in keeping the colon aligned so that stool can exit the colon via the rectum, and may prevent stool from getting trapped in a prolapsed pocket.

In certain embodiments, there is provided a method of supporting pelvic organ(s) in a subject with pelvic organ prolapse, the method comprising inserting the device of the present invention into the vagina of a subject in need thereof. In certain embodiments, the pelvic organ prolapse is stage 1 pelvic organ prolapse. In certain embodiments, the pelvic organ prolapse is stage 2 pelvic organ prolapse.

In certain embodiments, the intravaginal device of the present invention may be used in conjunction with pelvic floor therapy for treatment of pelvic organ prolapse and/or may help strengthen the pelvic floor muscles with regular use. Pelvic floor therapy includes but is not limited to pelvic floor exercises.

Overactive bladder and incomplete bladder emptying may be due to pelvic organ prolapse. Accordingly, in certain embodiments, the intravaginal device of the present invention may be used in a method of controlling female overactive bladder and/or controlling female incomplete bladder emptying.

An exemplary non-limiting method for the insertion of the device manually is detailed below.

1. Empty Bladder
2. If necessary, prior to insertion the removal strip is attached through the posterior hole and wrapped over the anterior wall (i.e. anterior bridge) within the notches. See FIGS. 5 to 7.
3. The device is cleaned before and after each use, for example by washing in warm water using unscented soap and rinsed.
4. The device may be inserted using a variety of techniques similar to inserting a tampon. The user should be relaxed and either sitting on a toilet with legs apart, or by standing and raising one leg (resting on something knee height), by squatting or laying down on the back with legs separated.
5. To insert, the device may either be wetted with warm water or if vaginal dryness occurs, a very small amount of water-based lubrication may be used.
6. The device is folded by compressing the central bridge (ring) with the forefinger and by squeezing the sides together. See FIGS. 9 and 10.
7. The anterior central bridge (ring) pointed away from the vaginal opening but facing up and the longer posterior end towards vaginal opening.
8. The folded device can now be gently inserted into the vaginal canal inwards and upwards until the bridge (ring) is no longer outside of the vaginal opening. The device should fit behind the pubic bone which should be felt as it passes under.

An exemplary non-limiting method for the insertion of the device using the assistive wand is detailed below.

1. Empty Bladder
2. If necessary, prior to insertion the removal strip is attached through the posterior hole and wrapped over the anterior wall (i.e. anterior bridge) within the notches. See FIGS. 5 to 7.
3. The device is cleaned before and after each use, for example by washing in warm water using unscented soap and rinsed.
4. The device may be inserted using a variety of techniques similar to inserting a tampon. The user should be relaxed and either sitting on a toilet with legs apart, or by standing and raising one leg (resting on something knee height), by squatting or laying down on the back with legs separated.
5. To insert, the device may either be wetted with warm water or if vaginal dryness occurs, a very small amount of water-based lubrication may be used.
6. The device is folded by compressing the central bridge (ring) with the forefinger and by squeezing the sides together. See FIGS. 9 and 10.
7. The device is placed in the bowl end of the assistive wand, and it is held in its collapsed position. The anterior central bridge (ring) pointed away from the vaginal opening but facing up and the longer posterior end towards vaginal opening.
8. The folded device which is held in the assistive wand can now be gently inserted into the vaginal canal inwards and upwards until the bridge (ring) is no longer outside of the vaginal opening. The device should fit behind the pubic bone which should be felt as it passes under. Once the said device is in the correct position the wand should be tipped upward to release the device from the wand and then the wand can be removed gently from the vagina.

An exemplary non-limiting method for manual removal of the device is detailed below.

1. To remove the device the user gets into the same position as used for insertion.
2. The removal strip is gently pulled down which will re-fold/collapse the device for easier removal.
3. Once the device is close to the vaginal opening the user's forefinger may be used to hook the side of the ring and gently pull downwards until the device is removed.

An exemplary non-limiting method for removal of the device using the assistive wand is detailed below.

1. To remove the device the user gets into the same position as used for insertion.
2. The hook end of the assistive wand is used to pull downward on either the removal strip by hooking at an opening on the removal strip, or by hooking on the device on the anterior bridge (ring). The device will re-fold/collapse when the removal strip is pulled.
3. Once the device is close to the vaginal opening the hook end of the assistive wand can be used to hook the side of the ring and gently pull downwards until the device is removed or the user's forefinger may be used to hook the side of the ring and gently pull downwards until the device is removed.
4. A small amount of sterile water-based lubricant or simply water may be used to wet inside vagina around the device and gently pull the removal strip. Alternatively, a finger or the hook end of the assistive wand can be inserted inside the vagina to squeeze the device's ring together to release any vacuum that has formed.

EQUIVALENTS

It will be understood by those skilled in the art that this description is made with reference to certain embodiments and that it is possible to make other embodiments employing the principles of the invention which fall within its spirit and scope.

The invention claimed is:

1. An intravaginal device comprising a hollow open-ended cylindrical body and a removal strip;
the body having a first end and a second end, an anterior wall and a posterior wall;
the body having a first notch in the first end of the anterior wall, and a second notch in the second end of the anterior wall wherein the first notch and the second notch are positioned in line and substantially at the midline of the anterior wall and forming a track for the removal strip;
the posterior wall comprising a lingulate-shaped extension, and an opening positioned substantially across from the first notch wherein the opening is adapted to receive therethrough the removal strip;
wherein the removal strip passes through the first notch, second notch and opening and when force is applied to the removal strip the anterior wall and the posterior wall are compressed together, and
wherein a first end of the removal strip is inserted through an opening in a second end of the removal strip thereby forming a loop which can be tightened when downward force is applied to the first end of the removal strip, thereby reducing a cross-sectional area of the body.

2. The intravaginal device of claim 1, wherein the body comprises a non-absorbent, flexible material.

3. The intravaginal device of claim 2, wherein the non-absorbent, flexible material comprises thermoplastic elastomers, or thermoplastic vulcanizates.

4. The intravaginal device of claim 2, wherein the removal strip comprises a non-absorbent flexible material, and when force is applied to the removal strip the anterior wall and the posterior wall are compressed together thereby reducing a cross-sectional area of the body.

5. The intravaginal device of claim 1, wherein the removal strip comprises a non-absorbent, flexible material.

6. The intravaginal device of claim 1, for use in aiding in the control of female urinary stress incontinence.

7. The intravaginal device of claim 1, for use in aiding pelvic organ prolapse.

8. The intravaginal device of claim 1, for use in aiding cystocele, urethrocele, uterine prolapse, vaginal vault prolapse, enterocele, rectocele, or a combination thereof.

9. A kit comprising the intravaginal device of claim 1 and instructions.

10. The kit of claim 9, further comprising an assistive wand.

11. The kit of claim 10, wherein the assistive wand comprises a hook.

12. The kit of claim 10, wherein the assistive wand comprises a bowl end that holds the intravaginal device in a collapsed position.

* * * * *